United States Patent
Evans

(10) Patent No.: US 7,430,043 B1
(45) Date of Patent: Sep. 30, 2008

(54) TURBIDIMETER IMPROVEMENTS

(76) Inventor: James M. Evans, 6991 Peachtree Ind., Bldg. 600, Norcross, GA (US) 30092

( * ) Notice: Subject to any disclaimer, the term of this patent is extended or adjusted under 35 U.S.C. 154(b) by 0 days.

(21) Appl. No.: 11/810,817

(22) Filed: Jun. 7, 2007

(51) Int. Cl.
*G01N 21/01* (2006.01)
*G01N 1/10* (2006.01)

(52) U.S. Cl. ........................ 356/244; 356/246
(58) Field of Classification Search .................. None
See application file for complete search history.

(56) References Cited

U.S. PATENT DOCUMENTS

| | | | |
|---|---|---|---|
| 4,810,090 A | * | 3/1989 | Boucher et al. ............... 356/39 |
| 5,446,544 A | * | 8/1995 | Beers ........................ 356/339 |
| 2003/0190262 A1 | * | 10/2003 | Blazewicz et al. ............ 422/94 |

* cited by examiner

*Primary Examiner*—Michael P Stafira
(74) *Attorney, Agent, or Firm*—Harry I. Leon; Vivian L. Steadman

(57) ABSTRACT

A turbidimeter with a pair of movable and stationary elements interconnected by a vertically-aligned hinge pin. Interior walls of these elements, when fully closed, define a cylindrical through passageway and an annular shelf which extends outwardly from its upper end. Otherwise, the stationary element, when the movable element has been pivoted away from it, defines one-half of the through passageway bisected lengthwise and a semi-annular shelf. Prior to use, a transparent cuvette can be slideably inserted sideways into the bisected through passageway and suspended there by protrusions on a cap threadedly engaged with the cuvette. The protrusions include a cap plate and an annular support shoulder which, in use, rests on the shelf. With its cuvette insertable sideways, an upflow sample cell, complete with supply and drain fittings fluidly connected to the cuvette, can be readily moved into and out of the turbidimeter to facilitate calibration procedures.

5 Claims, 3 Drawing Sheets

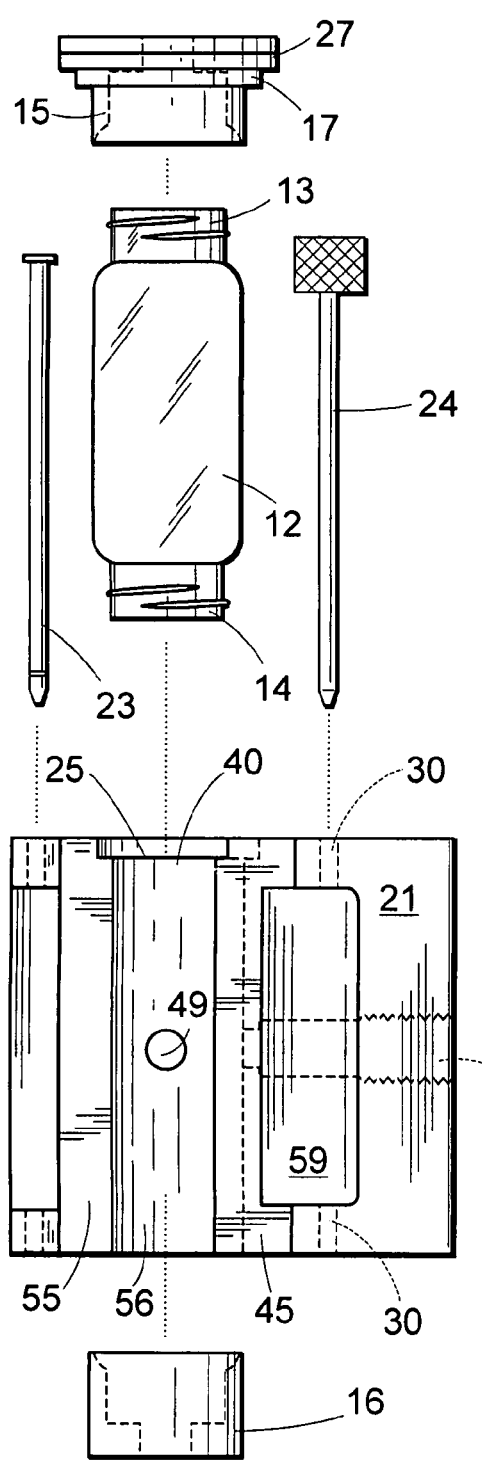
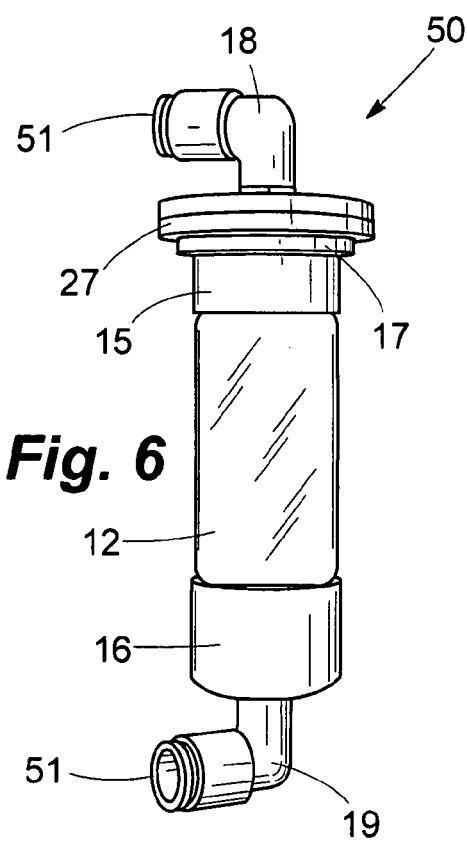
Fig. 6
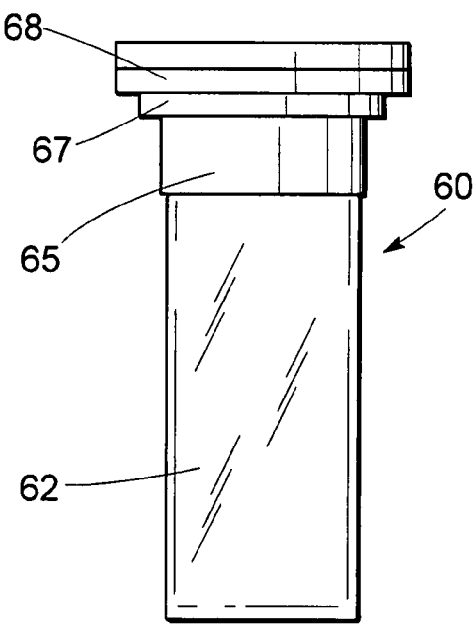
Fig. 5
Fig. 7

US 7,430,043 B1

TURBIDIMETER IMPROVEMENTS

FIELD OF THE INVENTION

This invention relates to turbidimeters and more particularly, to a flow-through sample cell and a holder for supporting the sample cell while its contents are subjected to nephelometric analysis.

BACKGROUND OF THE INVENTION

Nephelometric analysis is a well-known method of quantitative analysis in which the concentration of suspended matter in a liquid is determined by optical means. The method is based upon a comparison of the intensity of light scattered by a sample under defined conditions with the intensity of light scattered by a standard reference suspension. The higher the intensity of the scattered light is, the higher the turbidity.

Utilizing a nephelometer with a light source for illuminating the sample and at least one photoelectric detector with a readout device to indicate the intensity of the light scattered at right angles to the path of the incident light, a turbidimeter is usually designed to meet the specifications set forth in the EPA Guidance Manual entitled, "Method 180.1, Determination of Turbidity by Nephelometry". This manual specifies, among other things, that the turbidimeter be so designed that little stray light reaches the detector in the absence of turbidity. Instruments which are sufficiently sensitive to permit detection of a turbidity difference of 0.02 NTU or less in waters having turbidities less than 1 unit are considered to have met this criterion.

To this end, those previously proposing flow-through sample cells for use with a dynamic (continuously flowing) sample in an on-line version of the turbidimeter have kept the well of its cell port the same as if this instrument were being used to measure the turbidity of a static (non-flowing) sample of fixed volume. Only the sample cell and one or more of its inlet and outlet ports have been modified to accommodate a dynamic sample. In U.S. Pat. No. 5,475,486, for example, Paoli provides a standpipe which is connected to and extends upwardly from the bottom outlet port of his flow-through sample cell to a point above the top of the sample cell. Prior to use, the entire sample cell and the standpipe for most of its length are slideably inserted into the well of the cell port of a standard laboratory turbidimeter.

Further specifications as set forth in the EPA Guidance Manual describe procedures, using primary and secondary standard suspensions, to calibrate turbidimeters and the frequency with which their calibration should be verified. Unfortunately, in the case of prior art on-line turbidimeters, substantial quantities of very costly reagent must be used with each initial and subsequent primary calibration. A common approach is to use 1 liter sample reservoirs to purge flow-through sample cells, especially those having a single top discharge port. But even with Paoli's standpipe-augmented sample cell, reagent well in excess of that which would be required for the sample cell alone must be consumed because the standpipe siphons liquid away from the sample cell whenever one either partially fills the cell in order to flush any residual liquid from it or subsequently fills the cell sufficiently to actually calibrate it.

On the other hand, dead spaces in prior art sample cells which lack a bottom outlet port tend to collect settleable contaminants from the sample flow stream. These contaminants can then reenter the flow stream as a blob, giving rise to erroneous turbidity readings.

For use in a process such as water purification, it is highly desirable to utilize on-line turbidimeters capable of giving accurate real-time readings of the turbidity of process waters.

SUMMARY OF THE INVENTION

The object of the present invention is to provide an improved turbidimeter which not only can give accurate real-time turbidity readings and be calibrated using minimal quantities of primary and secondary standard suspensions but also is user friendly and inexpensive to purchase.

In accordance with the present invention, there is provided an improved sensor block and a flow-through sample cell with a transparent cuvette which is threadedly joined to an opaque upper cap. The sensor block includes first and second elements for holding the cuvette, as well as means for measuring the turbidity of a liquid such as processed drinking water, groundwater, sewerage, or industrial wastewater as it flows through the sample cell.

Interconnected by a hinge having a vertical axis about which the first element can be pivoted relative to the second element, interior walls of the first and second elements, when these elements are fully closed, defined an elongated through passageway and a channel. The bottom of the channel forms a narrow shelf which extends outwardly from the through passageway proximate with its upper end.

Slideably received within the through passageway, the transparent cuvette is held in suspension there by a cap plate and a support shoulder joined to the upper cap. Both the cap plate and the support shoulder which is disposed contiguous with it protrude outwardly from the upper cap. In use, the support shoulder, which has approximately the same height as that of the channel above the narrow shelf, is slip-fitted into the channel and rests on the narrow shelf. A close tolerance between the support shoulder and the channel keeps stray light from entering the top of the through passageway, as does the cap plate and its coverage of the juncture between the channel and the support shoulder.

Moreover, when the first and second elements are fully closed, their contiguous flat faces disposed proximate with and on either side of the through passageway are pressed together sufficiently firmly to form light-tight seams to keep stray light from entering the through passageway through these seams.

In the preferred embodiment, an opaque lower cap is also threadedly joined to the transparent cuvette. Portions of the upper and lower caps which are slideably receivable within the through passageway are cylindrical in shape, as are the interior walls of the first and second elements defining the through passageway. The transparent cuvette itself preferably has a cylindrically shaped midsection bounded by upper and lower end portions which are recessed inwardly from the outer side wall of the midsection and form a single, unitary piece with it. In assembled relation, the upper and lower caps are threadedly engaged with external threads defined by the upper and lower end portions, respectively. A close tolerance is maintained between the sides of the caps slideably received within the through passageway and the interior walls defining it in order to keep stray light from entering. The midsection of the transparent cuvette, on the other hand, has an outer diameter which is at most as large as the greatest outer diameter of said slideably received sides of the upper and lower caps.

Joined to an end portion of each cap which, in assembled relation, extends away from the transparent cuvette is an elbow or the like. In the preferred embodiment, elbows mounted on the lower and upper caps are fluidly connected to sample supply and drain lines, respectively, so that the sample flow stream enters through the bottom of the sample cell and leaves through its top. With such an upflow path for the sample flow stream, heavy contaminants which otherwise might settle out are kept in the flow stream and exit the sample cell without collecting on its bottom.

Prior to use, the first element of the sensor block can be swung open like a door. Once the first element has been rotated away from the second element so that their respective flat faces, which are otherwise contiguous when these elements are fully closed, are separated by a sufficiently large angle—an angle which in the preferred embodiment can be up to 180 degrees, the user can easily remove the flow-through sample cell and prepare it for a primary calibration procedure. In order to minimize the consumption of costly reagent used in such a procedure, plugs have been provided for stoppering the elbows mounted on the upper and lower caps. Instead of siphoning reagent away with a standpipe, for example, one can flush any residual liquid from the sample cell by partially filling only the sample cell itself. Likewise, only the sample cell needs to be filled in order to calibrate it.

Alternately, a closed sample cell, optically matched with the flow-through sample cell, can be used to perform a secondary calibration (calibration verification). The closed sample cell includes an upper opaque cap from which a cap plate and support shoulder extend outwardly. Like the support shoulder in the flow-through sample cell, the support shoulder in the closed sample cell is slip-fitted into the channel defined by the first and second elements of the sensor block when they are fully closed. Without stopping the sample flow stream, one simply swings open the first element, removes the flow-through sample cell, inserts the closed sample cell which has been prefilled with a suitable reagent, closes the first element, and takes the turbidity reading. Care must be taken to index and read both the closed and flow-through sample cells at their respective orientations which produce the lowest background blank value for each sample cell. But in general, this dry method of secondary calibration not only allows one to reuse the reagent employed as the standard but also to perform this procedure quickly.

BRIEF DESCRIPTION OF THE DRAWINGS

FIG. 5 is an elevation view of the stationary second element of the sensor block and of the flow-through sample cell according to FIG. 2, the door-like first element and the elbows connected to the sample cell having been removed for clarity of illustration, this view being partly exploded to show components of the sample cell, as well as the hinge and locking pins for the sensor block;

FIG. 6 is a perspective view of the flow-through sample cell according to FIG. 1 with its inlet and outlet ports plugged for calibration of the sample cell; and FIG. 7 is a perspective view of a closed sample cell which can be installed in the sensor block according to FIG. 2.

DETAILED DESCRIPTION OF THE PREFERRED EMBODIMENT

Figure 1:
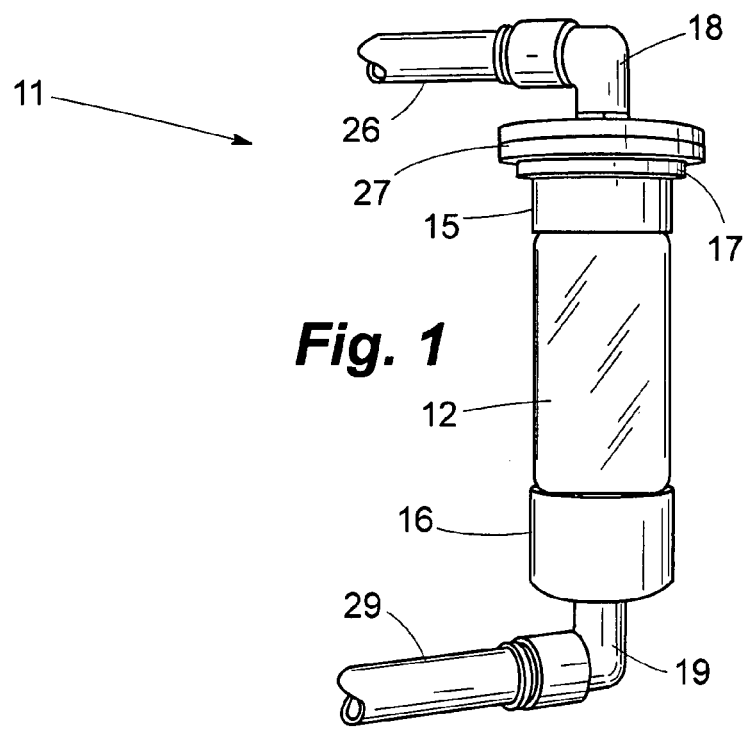
FIG. 1 is a perspective view of the flow-through sample cell according to the present invention.

In the drawings, a novel flow-through sample cell apparatus is indicated generally by the reference numeral 10. The apparatus 10 includes a sensor block 20 having two major components: a movable first element 22 and a stationary second element 21 which are hingedly connected together by a vertically-aligned hinge pin 23. As it is being pivoted about the pin 23, the first element 22 swings open like a door (FIG. 2).

Also included in the apparatus 10 is a flow-through sample cell 11 having a cuvette with a transparent midsection 12 and end portions 13, 14 which are formed as a single, unitary piece with the midsection. Threadedly engageable with external threads on the end portions 13, 14 are opaque caps 15, 16 which form water-tight seals with them. Protruding from the top edge of the upper cap 15 is a cap plate 27; and beneath it, is disposed a support shoulder 17 over which the cap plate is cantilevered.

In the preferred embodiment, the lower cap 16 and that portion of the upper cap 15 which is situated downwardly from the support shoulder 17 have cylindrical outer walls. Likewise, the midsection 12 of the cuvette which, in assembled relation, is juxtaposed between the upper and lower caps 15, 16 is also cylindrically shaped; but the outer diameter of the midsection is at most as large as the greatest outer diameter of the lower cap 16. In use, the midsection 12 of the cuvette is held in position within the sensor block 20 by the support shoulder 17 (FIGS. 2 and 3).

Figure 2:
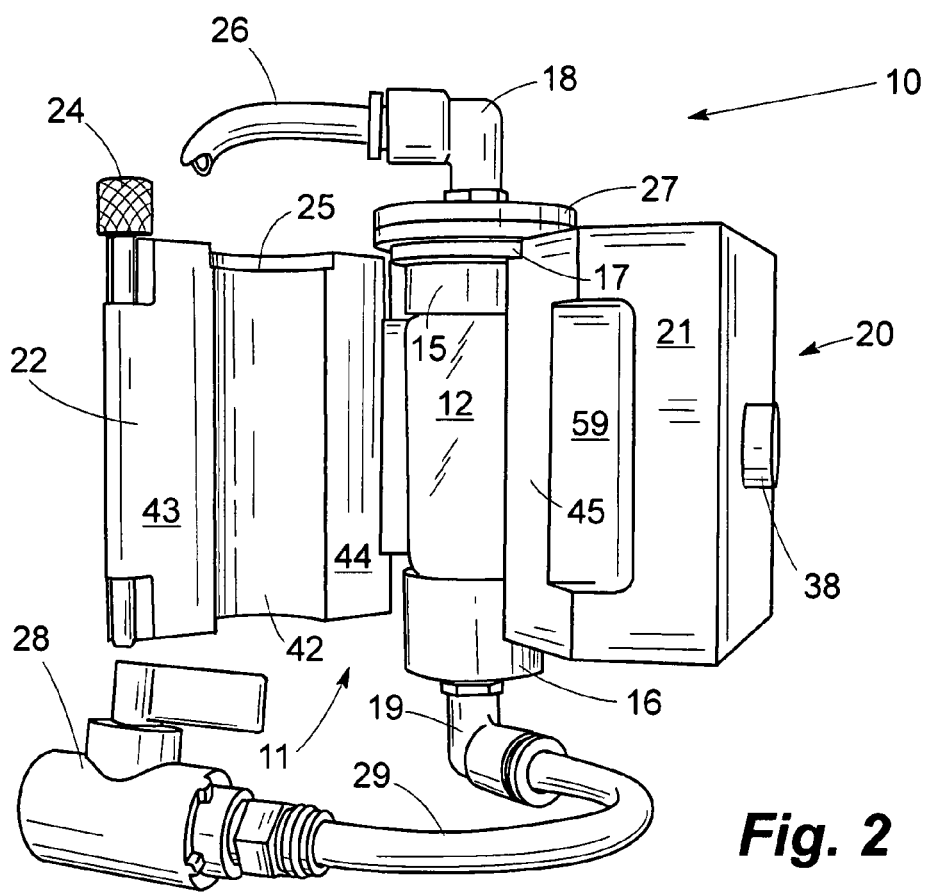
FIG. 2 is a perspective view of the sensor block and of the flow-through sample cell according to FIG. 1, the sample cell being shown installed in the sensor block and held in position there by the stationary second element while the hinged first element is temporarily swung open.
Figure 3:
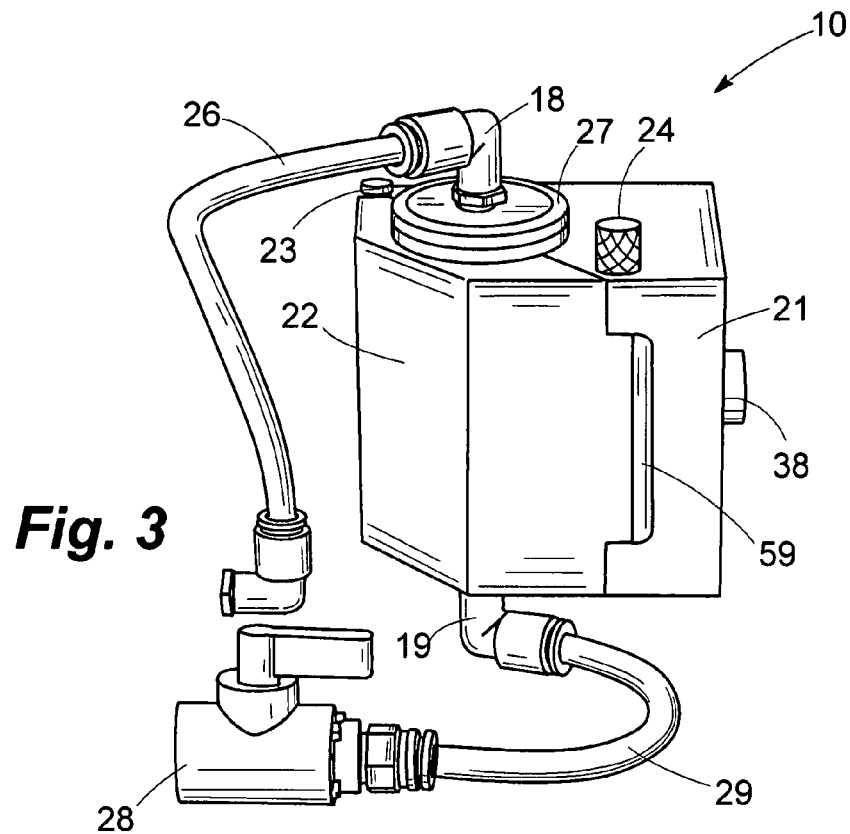
FIG. 3 is a perspective view of the sensor block and flow-through sample cell according to FIG. 2, the first and second elements of the sensor block being shown in their fully closed, working position.

As illustrated in FIGS. 2 and 5, first and second elements 22, 21 preferably have concave interior walls 42, 56 which, when these elements are fully closed, define an elongated through passageway 40. The radius of curvature of each interior wall 42, 56 is approximately equal to the radius of curvature of the lower cap 16 where its outer side wall is greatest in transverse cross-section. A close tolerance is maintained between said outer side wall and the interior walls 42, 56 in order to keep stray light from entering at the bottom of the through passageway 40 when the midsection 12 of the cuvette is held within the fully closed sensor block 20.

Figure 4:
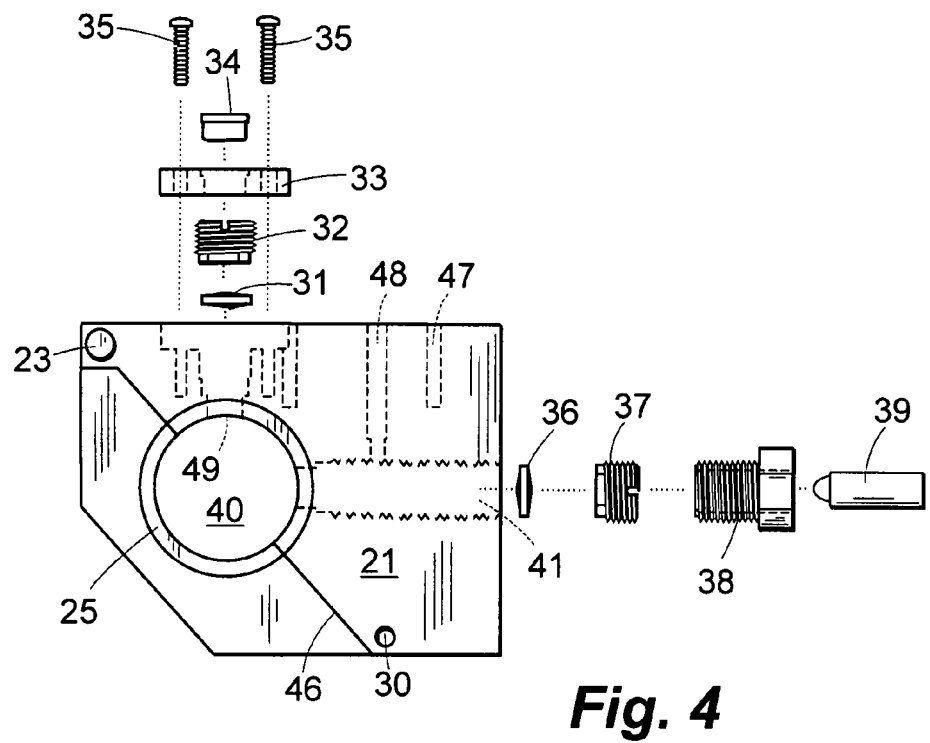
FIG. 4 is a top plan view of the sensor block according to FIG. 2, this view being partly exploded to show components used in the optical measurement of the turbidity of liquid in the sample cell.

Extending outwardly from the through passageway 40 proximate with its upper end is a channel with a concave interior face and a flat bottom which forms a narrow shelf 25 (FIGS. 2 and 4). In the preferred embodiment, the support shoulder 17 has approximately the same height as does the channel above the narrow shelf 25; and the shoulder has a convex exterior face with approximately the same radius of curvature as that of the concave interior face of the channel. In assembled relation, the support shoulder 17 is slip-fitted into the channel and rests on the narrow shelf 25. A close tolerance between the support shoulder 17 and the channel keeps stray light from entering the top of the through passageway 40, as does coverage of the juncture between the channel and the support shoulder provided by the cap plate 27 (FIG. 3).

Moreover, when the first and second elements 22, 21 are fully closed and held together by a locking pin 24, their contiguous flat faces 43, 45; 44, 55 disposed proximate with the through passageway 40 are pressed against each other sufficiently firmly to form light-tight seams 46 on either side of the through passageway (FIG. 4).

Means for retaining the locking pin 24 when it is holding the elements 22, 21 in their fully closed position includes a hole 30 and an elongated opening, alignable with the hole 30, defined by the second and first elements, respectively. Situated distal from the hinge pin 23 and extending vertically between top and bottom cutouts defined by the first element 22, the elongated opening has approximately the same transverse cross-section as does the hole 30. In the preferred embodiment, when the first and second elements 22, 21 are fully closed, a latchable portion of the first element which extends from the top cutout to the bottom cutout is seated in a recess 59 defined by the second element 21 in such a way that both the hole 30 and the elongated opening can slideably receive the locking pin 24 at the same time (FIGS. 2 and 3).

Mounted on the lower and upper caps 16, 15 and fluidly connected to sample supply and drain lines 29, 26, respectively, are elbows 19, 18 (FIGS. 2 and 3). A valve 28 on the sample supply line 29 can be used to shut off flow of the sample stream. A debubbler (not shown) is preferably employed upstream of the valve 28 to remove entrained air bubbles which would otherwise interfere with turbidity measurements. Constant head pressure from the debubbler, from which only a slipstream is taken off to feed the sample cell 11, insures a constant flow, which is preferably in the range of 100 to 1000 milliliters per minute, to this sample cell. In use, the sample stream, as it follows an upflow path through the sample cell 11 from the lower elbow 19 to the upper elbow 18, has sufficient velocity to keep heavy contaminants from settling out of the flow stream; and they exit the sample cell without collecting on its bottom. A suitable debubbler, for which patent protection is currently being sought, has recently been developed by Chemtrac Systems, Inc. of Norcross, Ga.

Located within the stationary second element 21 of the sensor block 20 are both a light source 39 and a photodiode 34; these key components which are commonly used in measuring the turbidity of a liquid sample are mounted within an elongated tunnel 41 and a sensor mounting hole 49, respectively (FIGS. 4 and 5). Both of them are defined by the stationary second element 21, and the tunnel 41 and mounting hole 49 have longitudinal centerlines which are permanently disposed perpendicularly to each other. Originating with the light source 39, a light beam can be directed at the midsection 12 of the transparent cuvette when it is suspended by the shoulder 17 within the passageway 40. The light beam, once it has struck a liquid suspension within the cuvette, must then be scattered at right angles to the tunnel 41 before light from the beam can be detected by the photodiode 34.

In addition to the light source 39, which is preferably a tungsten lamp, its retainer 38, a focusing lens 36 and a lens retainer 37 are mounted in the tunnel 41 (FIG. 4). Likewise, the sensor mounting hole 49 holds not only photodiode 34 but also a diode retainer 33, a lens 31, and its retainer 32, all of which are rigidly attached to the second element 21 by a pair of fasteners 35 (FIG. 4). Means for checking the intensity of the light source 39 includes a lamp intensity measurement photodiode (not shown) mounted in a hole 48. As shown in FIG. 4, the hole 48 intercepts the tunnel 41 at a point between its entrance into the through passageway 40 and the light source 39.

Included in sensor electronics for the apparatus 10 are the light source 39, the photodiode 34, the photodiode for measuring the lamp intensity, and signal conditioning electronics. The signal from the photodiode 34, which measures the intensity of light scattered through 90 degrees from the tunnel 41, is amplified through various gain stages with the output of each stage being input to a multiplexer IC. An auto-ranging feature of the signal conditioning electronics determines which gain stage output to pass through the multiplexer for further processing to use ultimately for display and various other outputs.

The signal from the lamp intensity measurement photodiode is amplified through two gain stages to a preset value. Significant deviation from this preset value generates an alarm indicating that the lamp intensity has changed and lamp replacement or re-calibration may be required.

As is best seen in FIGS. 2 and 5, the stationary element 21 and the movable element 22 each define, when the sensor block 20 is open, an elongated concavity which in transverse cross-section is equal to one-half of that of the through passageway 40, as well as a semi-annular segment of the shelf 25. Prior to use and with the movable element 22 pivoted away from the stationary element 21, the transparent cuvette of a flow-through sample cell 11 can be slideably inserted sideways into the elongated concavity of the stationary element. Simultaneously, the support shoulder 17 can be slid onto the semi-annular segment of the shelf 25. Once the cuvette has been inserted as far as possible into the elongated concavity and approximately one-half of the support shoulder 17 rests on the shelf segment, the support shoulder and the cap plate 27 act in concert to hold the cuvette in suspension downwardly of the shelf segment until the sensor block 20 can be fully closed.

With its cuvette insertable sideways into the elongated concavity of the stationary element 21, the upflow sample cell 11, complete with supply and drain fittings 19, 18 fluidly connected to the cuvette, can be readily moved into and out of the sensor block 20 to facilitate secondary calibration procedures. Moreover, close coupling between the lower and upper caps 16, 15 and the elbows 19, 18, which, in use, are preferably mounted just outside of the distal ends of the through passageway 40, reduces the amount of dead volume which must be filled with a costly primary standard suspension each time a primary calibration, which, unlike a secondary calibration, requires the supply and drain lines 29, 26 be disconnected from the apparatus 10, must be performed.

As recommended in the EPA Guidance Manual, on-line turbidimeters such as the apparatus 10 should be calibrated using a primary suspension standard initially and at least every three months thereafter to prevent instrument drift, unless more frequent primary calibrations are needed as determined by secondary calibration procedures. In general, EPA guidelines call for secondary calibrations to be performed at least monthly; but in certain situations such as those in which an on-line turbidimeter is used to monitor a combined filter effluent, they may need to be conducted on a weekly basis.

By disconnecting the supply and drain lines 29, 26 and plugging the closely coupled elbows 19, 18 with stoppers 51, one can readily convert the dynamic sample cell 11 into a static sample cell 50 (FIG. 6). Importantly, the dead volume in the case of the static sample cell 50 is but a small fraction of the volume which its transparent cuvette holds—the latter volume preferably measuring only about 30 milliliters, so that by using the apparatus 10, an operator can greatly reduce the amount of primary standard reference suspension needed to calibrate the sensor block 20/sample cell 50 combination over that which would be consumed with a conventional on-line turbidimeter. Alternately, one can temporarily replace the caps 15, 16 with permanently sealed upper and lower caps (not shown) and achieve similar cost savings.

Once sample flow through the sample cell 11 has been stopped, one can perform a primary calibration with the apparatus 10 by unlocking and opening the sensor block 20, removing the flow-through sample cell 11, disconnecting the supply and drain lines 29, 26, and inserting stoppers 51 in their stead. One next proceeds to remove the stoppered flow-through cap 15 and flush and later refill the open cuvette with zero NTU standard. Preferably, only about 15 milliliters of zero NTU standard is used for the flush and 30 milliliters of this same standard during refill. After the cuvette has been sealed with the stoppered cap 15, the cuvette is slid sideways into the concavity of the stationary element 21 and then rotated in place until indexing marks (not shown) on the cap plate 27 and the stationary element are brought into alignment. Adjustment of the output from the sensor electronics of the apparatus 10 follows. Using suitable digital communications components/software such as RS485 (Modbus RTU & Modbus ASCII), Ethernet (Modbus TCP), and Bluetooth, one adjusts this output until the measured turbidity, as shown on an electronic display/keypad (not shown) or the like, is "0 NTU" and thereby completes the calibration of the zero point for the apparatus 10. The primary calibration procedure is then repeated using a 2 NTU, 10 NTU or 100 NTU standard, depending upon the range of turbidity normally expected for the sample flow; and the span is set by adjusting the sensor electronics output until the measured turbidity reads either "2 NTU", "10 NTU" or "100 NTU", as appropriate for the particular primary standard then filling the cuvette of the sample cell 50.

With secondary calibrations, on the other hand, one need not stop sample flow through the sample cell 11. Instead of converting it to a stoppered sample cell 50 and then flushing and filling the latter with a secondary suspension standard, one can use a closed static sample cell 60 which has a transparent cuvette 62 optically matched to the transparent cuvette of the sample cell 11 and prefilled with a secondary standard of known NTU value. In the preferred embodiment, the sample cell 60 includes an opaque upper cap 65 joined, in use, to the cuvette 62 by a water-tight seal. Protruding outwardly from the upper cap 65 is a cap plate 68 and a support shoulder 67 which, in their respective transverse cross-sections and juxtaposition to each other, approximate that of the cap plate 27 and support shoulder 17 in the sample cell 11.

An actual secondary calibration is carried out by removing the locking pin 24 from the sensor block 20, swinging open the movable element 22, removing the flow-through sample cell 11, slipping the cuvette 62 sideways into the concavity defined by the stationary element 21 while simultaneously sliding the support shoulder 67 onto the semi-annular segment of the shelf 25, rotating the sample cell 60 in place until indexing marks (not shown) on the cap plate 68 and the stationary element are brought into alignment, closing the movable element 22, reinserting the locking pin 24, and taking the turbidity reading. If the NTU value indicated on the electronic display for the apparatus 10 is within +/−10 percent of the known NTU value of the secondary standard as preferably stated on the cuvette 62, then the secondary calibration (calibration verification) is complete; and one can reinstall the flow-through sample cell 11 in the sensor block 20. Otherwise, a primary calibration must be performed. When only secondary calibration is required, the dynamic sample cell 11 can be removed and the static sample cell 60 installed in about 1 minute. Moreover, the static sample cell 60 uses as little as 50 milliliters of secondary standard and can be reused repeatedly to perform secondary calibrations.

Primary and secondary suspension standards suitable for calibrating the apparatus 10 include Amco Clear® standards available commercially from GFS Chemicals.

I claim:

1. An apparatus for measuring the turbidity of a liquid sample, which comprises:

(a) a sample cell including a cuvette and an opaque upper cap which is threadedly engageable with the cuvette, a midsection of the cuvette having a transparent wall with a generally cylindrical outer surface which, in assembled relation, is disposed downwardly of the upper cap; and (b) a sensor block having first and second elements and a vertically-aligned hinge pin, the first element being movably interconnected to the second element by the hinge pin; the first and second elements having first and second concave walls which define first and second elongated concavities, respectively, each of which is approximately semi-circular in transverse cross-section and extends vertically; the first and second concave walls, when the first and second elements are fully closed, defining an elongated through passageway, the through passageway and the midsection of the cuvette being approximately circular in transverse cross-section; the radius of curvature of each of the concave walls being at least slightly greater than the radius of curvature of the outer surface of the transparent wall of the midsection of the cuvette, so that, in use, the midsection can be held within the through passageway; a portion of the midsection being slideably insertable sideways into the second elongated concavity when, prior to use, the first element has been pivoted away from the second element through at least as large an angle as is required to pass the midsection of the cuvette upright, between the first and second elements, from points on the second element which are distal from the hinge pin to the second concave wall.

2. The apparatus according to claim 1, which further comprises means for holding a portion of the midsection of the cuvette in a fixed position within the second concavity while the first and second elements of the sensor block are open, the holding means including an annular support shoulder which is rigidly attached to the upper cap and extends outwardly therefrom; the second element defining a semi-annular shelf which extends outwardly from the upper end of the second concavity, part of the support shoulder resting on the semi-annular shelf when said portion of the midsection is held within the second concavity.

3. In a nephelometer in which a light source sends a beam of directed light through the transparent wall of a sample cell and in which a detector is mounted at 90 degrees to the beam of directed light, wherein the improvement comprises:

(a) a sensor block having first and second elements and a vertically-aligned hinge pin, the first element being movably interconnected to the second element by the hinge pin; the second element defining first and second elongated passageways which extend horizontally, the longitudinal centerline of the first elongated passageway being disposed perpendicularly to the longitudinal centerline of the second elongated passageway; the light source and the detector being mounted within the first and second elongated passageways, respectively; and (b) the first and second elements having first and second concave walls which, when the first and second elements are fully closed, define a third elongated passageway which extends vertically and which is intercepted by the first and second elongated passageways; the transparent wall of the sample cell and the third passageway being both elongated and approximately circular in transverse cross-section; the radius of curvature of each of the concave walls being at least slightly greater than the radius of curvature of the outer surface of the transparent wall, so that, in use, the transparent wall of the sample cell can be held upright within the third through passageway; the longitudinal centerlines of the first and second elongated through passageways crossing within space surrounded by the transparent wall when the sample cell is so held.

4. The improvement according to claim 3, which further comprises the second concave wall defining a second elongated concavity which is approximately semi-circular in transverse cross-section and extends vertically; a portion of the transparent wall of the sample cell being slideably insertable sideways into the second elongated concavity when, prior to use, the first element has been pivoted away from the second element through at least as large an angle as is required to pass the transparent wall of the sample cell upright, between the first and second elements, from points on the second element which are distal form the hinge pin to the second concave wall.

5. The improvement according to claim 4, which further comprises:

(a) the sample cell having an opaque upper cap which is connected to the transparent wall in such a way as to from a water-tight seal;

(b) an annular support shoulder which is rigidly connected to the upper cap and extends outwardly therefrom; and (c) the second element defining a semi-annular shelf which extends outwardly from the upper end of the second concavity; the annular support shoulder being slideable along the semi-annular shelf, while the first element is pivoted away from the second element, once said portion of the transparent wall has been slideably inserted sideways into the second concavity.

* * * * *